United States Patent [19]

Campbell

[11] Patent Number: 4,581,011

[45] Date of Patent: Apr. 8, 1986

[54] PREPACKAGED MANUAL ADMINISTRATION SET FOR ACUTE PERITONEAL DIALYSIS IN INFANTS AND ADULTS

[75] Inventor: Fern G. Campbell, Charlottesville, Va.

[73] Assignee: The University of Virginia Alumni Patents Foundation, Charlottesville, Va.

[21] Appl. No.: 605,678

[22] Filed: Apr. 30, 1984

[51] Int. Cl.$^4$ .............................................. A61M 1/00
[52] U.S. Cl. ...................................................... 604/29
[58] Field of Search .................................... 604/27–34, 604/131, 141; 128/DIG. 12

[56] References Cited

U.S. PATENT DOCUMENTS 4,412,917 11/1983 Ahjopalo ............................... 604/29

FOREIGN PATENT DOCUMENTS 1964735 7/1971 Fed. Rep. of Germany ........ 604/29
1546839 11/1968 France ................................... 604/29

Primary Examiner—John D. Yasko
Attorney, Agent, or Firm—James C. Wray

[57] ABSTRACT

A manual administration set for acute peritoneal dialysis in infants and adults is disclosed which has a minimum of connections so as to minimize risk of infection and includes a heating means for patient comfort and performance of more efficient dialysis. The prepackaged set up for infants and small children contains volutroles within the tubing for the measurement of small volumes to be used in dialysis. The set up is capable of handling from one container up to four containers and will have sufficient tubing length to allow for any amount of movement of the child or the adult patient.

8 Claims, 2 Drawing Figures

PREPACKAGED MANUAL ADMINISTRATION SET FOR ACUTE PERITONEAL DIALYSIS IN INFANTS AND ADULTS

BACKGROUND OF THE INVENTION

The invention is related to the art of liquid purification or separation by diffusion, especially with respect to biological fluids. The apparatus contains inlets and outlets for diverse streams leading to and from the abdominal cavity where the semipermeable membrane used for dialyzing the biological fluid is the actual peritoneum of the individual. The prior art allows for the administration of dialysis fluid to the abdominal cavity and for the draining of the fluid once it has washed the peritoneum for a sufficient period of time. However, prior art does not include any heating unit. Previous studies state that heating of fluid to body temperature increases the efficiency of dialysis and promotes patient comfort. This is even more important in infants who have difficulty in maintaining and regulating body temperatures. Current methods of heating fluid in water bath have been studied, and increased risks of contamination has been documented with the heating of the fluid in the water bath. There is also no method of allowing accurate measurement of small volumes to be used in infants and small children with peritoneal dialysis. Such volumes need to be in the 25-100 ml range. Prior art also has allowed for either single or Y-type connections which allow at a maximum of up to two containers per set up. Thus, at times, the frequent opening of the system is necessary to effect a more desirable dialysis, which has the consequential increase in the rate of infection and nursing time required. Also, prior art is deficient in tubing length as the length of tubing is insufficient to allow any amount of movement of child or adult.

The nursing time now spent in assembling the current system, adding a variety of additional tubes, heating unit and drainage bag, (currently nine to ten different connections which can accidentally disconnect) could be eliminated with a preconnected tubing set complete with fluid-warmer system and drainage bag. Therefore, it is an object of the invention to provide a fluid-warmer which would allow safe and accurate warming of fluid just prior to instilling into patient. It is also an object of the invention to adjust to infants and their needs in dialysis by allowing for accurate measurement of volumes of dialysate to be administered.

Yet another object of the invention is to permit a two- or four-container system to be administered, thus decreasing the number of disconnections or opening of the system required, which, in turn, would decrease infection rates and nursing time.

Still another object of the invention is to provide sufficient tubing length to allow for any amount of movement by the child or the patient.

Still another object of the invention is to provide a resealable rubber injection port near the drainage bag to allow ease in obtaining fluid cultures which would not require opening of the system as is currently in practice.

SUMMARY OF THE INVENTION

The invention is a prepackaged manual administration set up for acute peritoneal dialysis in infants and adults. The invention comprises one to four spikes, each of which would attach to a dialysate fluid bag with large-bore tubing leading from the spikes in the bag. This tubing is connected to a Y connector, as in the case of adults, or to a 100 cc volutrole, as in the case of children, and in which case large-bore tubing would lead from the volutrole to a Y connector. Just before the large-bore tubing connects to the Y connector, there is situated a clamp upon a tubing in order to control the flow of the fluid leading through the tubing. The Y connector receives up to two large-bore tubings leading from volutroles or directly from the dialysate bags. The Y connector leads directly to a second Y connector which has a branch either covered by a protective cover or may itself lead to one or two more large-bore tubings leading from bags of dialysate. It is the second Y connector which allows for the multiplicity of containers to be used in the dialysis process.

The second Y connector is connected to a large-bore tubing that leads to a fluid warmer. This fluid warmer heats the fluid within the tube and allows the tubing to leave the fluid warmer and the tubing then connects to a third Y connector. Before arriving at the third Y connector, the tube is subject to a roller clamp which is capable of controlling the flow within.

The other branch of the third Y connector has large-bore tubing flowing toward the drainage bag. That large-bore tubing has between the third Y connector and the drainage bag a roller clamp and a resealable rubber injection port from which to obtain cultures. The remaining branch of the Y connector has a 30" extension upon it which leads to the peritoneal dialysis catheter. The catheter, of course, is inserted into the patient.

The blood fluid warmer can be any one of a number of commercially available fluid warmers, including but not exclusively, the American Medical Systems models: DW-1000, DW-1000A, DW-1220, DW-1000D.

The preferred heater has an adjustable temperature thermostat controlled heating plate around which a flat thin-walled conduit bag is secured. The conduit bag is part of the permanently connected system of the present invention.

DESCRIPTION OF THE PREFERRED EMBODIMENT

Figure 1:
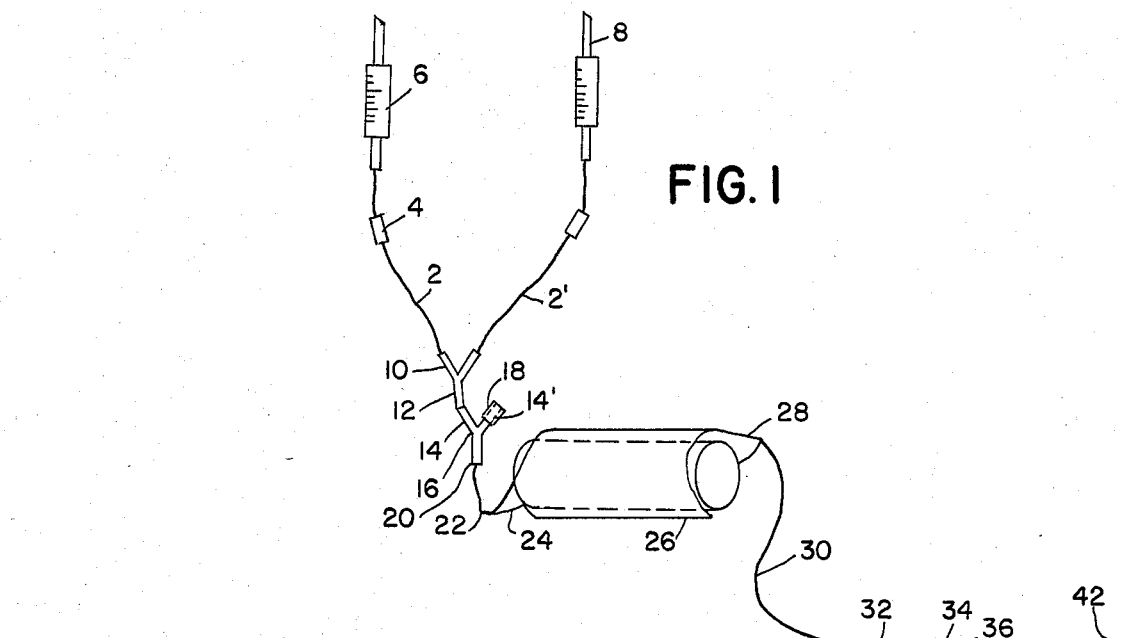
FIG. 1 is a schematic representation of a preferred embodiment of the invention for use with acute dialysis of infants and small children.

Peritoneal dialysis affords a very attractive alternative to the more harsh hemodialysis. Hemodialysis is the more drastic method of removing toxic substances from the body because of the relative immobility of the patient during the procedure, as well as the extreme discomfort experienced during and after the dialysis. In addition, hemodialysis requires expensive machinery and constant nursing care.

Peritoneal dialysis, if possible, provides a far better world for the dialysis patient. It is less expensive, less immobilizing, more comfortable and generally more conducive to maintaining some semblance of a lifestyle.

The invention enhances peritoneal dialysis by making it even less expensive, more comfortable and less immobilizing than before. The invention provides a prepackaged manual administration set up for acute peritoneal dialysis. The improvement over prior art is such that significant nurse time is eliminated by having the fully assembled system ready to go. Prior art is such that a nurse spends quite a bit of time assembling the tubing which allows for more risk of infection due to the system being open and exposed. Prepackaging and preconnecting alone cuts down on nurse time and risk of infection.

The invention is a mode especially adapted for infants and children which takes into account the smaller volumes of dialysis solution to be used in the process.

The volutroles located on the tubing leading from the dialysis solution allows for measuring aliquots up to 100 cc in volume to be administered to the patient. Heretofore, this has been a problem, and, thus, acute peritoneal dialysis has not been as attractive an alternative to hemodialysis with children as it has been with adults.

The invention allows for two to four containers of dialysis solution to be administered without any opening of the system. This is due to two Y connectors arranged in tandem, connected to large-bore tubing leading from the dialysis solution containers. Tubing from two containers connect to the first Y connector, which, in turn, is connected to a second Y connector. The second Y connector has one branch available, with a protective cover, for attachment to tubing leading from a third dialysis solution container or to another Y connector which can handle two more dialysis solution containers.

The tubing leading from the Y connectors then goes through a blood/fluid warmer of which there are several commercially available. (American Medical Systems or American Hamilton Blood/Fluid Warmer Models: DW-1000, DW-1000A, DW-1220, DW-1000D). Prior art discloses the use of a water bath to heat up the dialysis solution, but this has been impractical due to the level of infection occurring. A method is needed to obviate the danger of the water bath and still heat up the dialysis solution. It is known that diffusion and dialysis in general is more efficient if the fluid is at body temperature.

The patient is also much more comfortable with the dialysis solution being administered at body temperature.

The blood fluid warmers provide the heat with no risk of compromising the sterile field.

Once the tubing leaves the warmer, it connects to another Y connector which leads both to the peritoneal dialysis catheter and, thus, to the patient, as well as to a drainage bag.

Since the process of acute peritoneal dialysis must be monitored extensively for infection, a resealable rubber injection port is located on the tubing leading to the drainage bag from which samples of the dialysate may be taken and cultured.

Clamps are connected at various points along the tubing to stop or control flow. In the adult mode, clamps are located on the large-bore tubing just below the dialysis solution container. These clamps control the flow of solution to the patient. In the infant mode, the clamps are located just below the volutroles on the tubing. There are roller clamps located on the tubing leading to the third Y connector which leads to the patient. The roller clamp on the tubing bringing the dialysis solution is located just before the connection to the Y connector. This is to stop the flow to the patient. The roller clamp on the tubing leading to the drainage bag is also located near the Y connector and will allow for dialysate solution to pass from the body of the patient to the drainage bag.

The third Y connector has a 30" extension on the branch leading to the peritoneal dialysis catheter to allow for more mobility. The lengths of tubing used in the invention are large enough to allow for considerable mobility while enduring the dialysis procedure.

In the preferred embodiment, all that would be needed to perform a sterile acute peritoneal dialysis is the requisite number of dialysis solution containers, the prepackaged manual administration set up and a patient. The nurse would unpackage the set up, hook the tubing up to the containers into the patient and start the dialysis solution down the tubing to the warmer. When a sufficient volume is flowed through the warmer and into the patient, the dialysis solution is stopped at the third Y connector, where both clamps are operating to stop the flow to and from the patient. Upon waiting the necessary period of time, the roller clamp on the tubing leading to the drainage bag is opened, and the dialysate is allowed to leave the patient and may be sampled before entering the drainage bag for later culturing and analysis.

Once the dialysate has drained, then the roller clamp on the tubing leading to the drainage bag is adjusted to stop the draining and the roller clamp upon the tubing leading from the dialysis solution may be released to allow for more dialysis.

As shown in FIG. 1, the present invention, the acute peritoneal dialysis kit, is generally indicated by the numeral 1. Kit 1 includes permanently interconnected tubing 2 with clamps 4 leading to 100 cc volutroles 6 with spikes 8. Y connector 10 has inlets permanently connected to tubing 2 and 2'. The outlet 12 of Y connector 10 is permanently connected to inlet 14 of Y connector 16. The other inlet 14' of the Y connector is covered with a protective cover. The protective cover 18 may be removed to connect the outlet of another Y connector similar to 10 to the inlet 14' to provide a four-container operation.

Outlet 20 of Y 16 is permanently connected to a tubing 22 which leads to the inlet 24 of thin-walled warmer bag 26. The outlet 28 of the thin-walled warmer bag 26 is permanently connected to a tube 30. A roller clamp 32 controls flow through tube 30. Tube 30 is permanently connected to the inlet 34 of a Y connector 36. The outlet 38 of the Y connector 36 is permanently connected to a 30" extension 40 which has a connector 42 at its distal end for connecting to a connector of a catheter in the patient. Y connector 36 has an outlet 44 permanently connected to a tube 46. A roller clamp 48 controls flow through the tube 46. A resealable rubber injection port 50 is permanently connected to tube 46 to provide for the aspiration of samples for cultures.

The distal end of tube 46 is permanently connected to inlet 52 of drainage bag 54. The drainage bag has an outlet 56 with a clamp 58 to control flow of collected fluid from the drainage bag.

Figure 2:
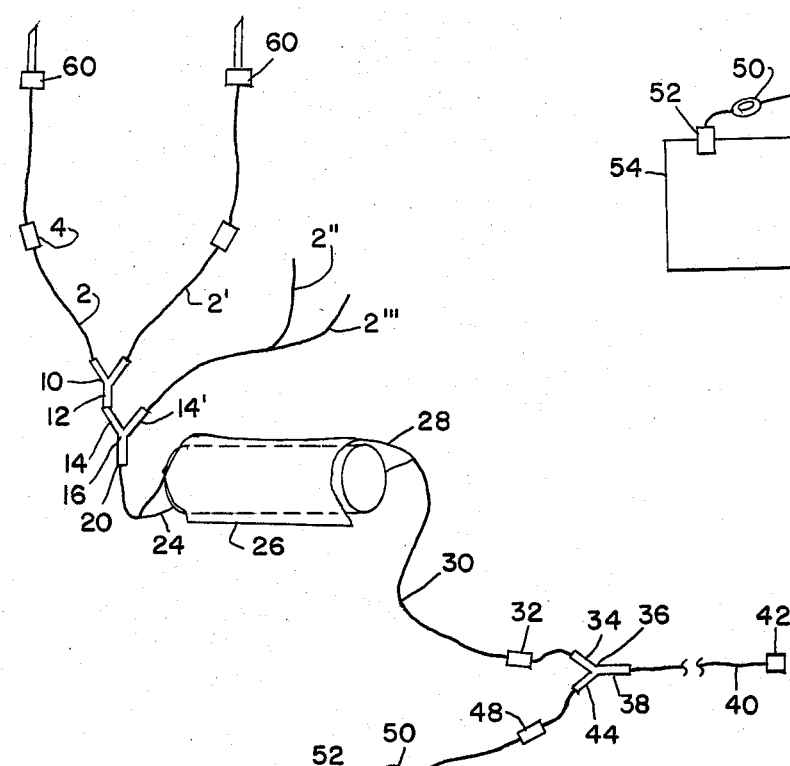
FIG. 2 is a schematic representation of a preferred embodiment of the invention for use with adults.

In FIG. 2, similar elements are marked with similar numbers. Tubes 2 and 2' have permanently attached spikes 60 and 60' for inserting in large liter or half liter bags. In the adult modification, tubes 2" and 2'" with spikes which are not shown are permanently attached to inlet 14' of connector 16 to provide flow bag operation.

In the preferred embodiment, the present system is changed every 24 hours. When used with an adult, if more than four liters are required, spikes 60 are concurrently removed from empty bags and placed in new bags under sterile conditions.

I claim:

1. A prepackaged manual administration set for acute peritoneal dialysis in infants comprising one, two, three or four spikes with large-bore tubing leading therefrom connected to 100 cc volutroles which are, in turn, connected to large-bore tubing leading therefrom, said large-bore tubing leading to and from a clamp to control flow situated on the tubing leading from the volutroles, said large-bore tubing then connected to a Y connector which accepts two large-bore tubings and, in turn, connects to a second Y connector which may have one branch of the Y protectively covered or attached to other tubing such that up to four containers with volutroles may be connected, the second Y connector is connected to one large-bore tubing leading to a fluid-warming means, upon leaving the fluid warmer, the large-bore tubing is subjected to a roller clamp with large-bore tubing leading therefrom and connected to a third Y connector, connected to another branch of the third Y connector is another large-bore tubing leading therefrom which is subjected to a roller clamp not too distant from the third Y connector with the large-bore tubing having a resealable rubber injection port situated on the tubing just before connecting to a drainage bag, the last branch of the third Y connector is connected to a 30" extension which is connected to a peritoneal dialysis catheter.

2. A prepackaged manual administration set for acute peritoneal dialysis in adults comprising one, two, three or four spikes with large-bore tubing leading therefrom connected to large-bore tubing with a clamp situated on the tubing to control flow, said tubing connected to a Y connector which accepts two large-bore tubings and, in turn, connects to a second Y connector which may have one branch of the Y protectively covered or attached to other tubing such that up to four containers with spikes may be connected, the second Y connector is connected to one large-bore tubing leading to a fluid-warming means, upon leaving the fluid warmer, the large-bore tubing is subjected to a roller clamp with large-bore tubing leading therefrom and connected to a third Y connector, connected to another branch of the third Y connector is another large-bore tubing leading therefrom which is subjected to a roller clamp not too distant from the third Y connector with the large-bore tubing having a resealable rubber injection port situated on the tubing just before connecting to a drainage bag, the last branch of the third Y connector is connected to a 30" extension which is connected to a peritoneal dialysis catheter.

3. A manual administration set up for acute peritoneal dialysis in infants comprising tubing means connected to dialysis fluid such that said tubing is subject to volutroles or volume control, whereupon the tubing is such that it may accept up to four containers with four separate volutroles, said container and volutroles being connected by Y connectors to a single large-bore tubing leading therefrom and through a fluid warmer, whereupon said large-bore tubing leading from the fluid warmer connects to a Y connector which would control the warm fluid going into the individual, as well as fluid running out of the individual and to a drainage bag.

4. A manual administration set up for acute peritoneal dialysis in adults comprising tubing means connected to dialysis fluid, wherein the tubing is such that it may accept up to four containers with four separate spikes, said container and spikes being connected by Y connectors to a single large-bore tubing leading therefrom and through a fluid warmer, whereupon said large-bore tubing leading from the fluid warmer connects to a Y connector which would control the warm fluid going into the individual, as well as fluid running out of the individual and to a drainage bag.

5. The apparatus of claim 1 where the blood fluid warmer further comprises the systems of American Medical Systems or American Hamilton blood fluid warmer models DW-1000, DW-1220, DW-1000A and DW-1000D.

6. The apparatus of claim 2 where the blood fluid warmer further comprises the systems of American Medical Systems or American Hamilton blood fluid warmer models DW-1000, DW-1220, DW-1000A and DW-1000D.

7. The apparatus of claim 3 where the blood fluid warmer further comprises the systems of American Medical Systems or American Hamilton blood fluid warmer models DW-1000, DW-1220, DW-1000A and DW-1000D.

8. The apparatus of claim 4 where the blood fluid warmer further comprises the systems of American Medical Systems or American Hamilton blood fluid warmer models DW-1000, DW-1220, DW-1000A and DW-1000D.

* * * * *